(12) United States Patent
Almario Garcia et al.

(10) Patent No.: US 6,844,335 B2
(45) Date of Patent: Jan. 18, 2005

(54) 2-AMINO-3-(ALKYL)-PYRIMIDONE DERIVATIVES AS GSK3.β.INHIBITORS

(75) Inventors: Antonio Almario Garcia, Chantenay Malabry (FR); Ryoichi Ando, Tokyo (JP); Keiichi Arimoto, Tokyo (JP); Fumiaki Uehara, Tokyo (JP); Adrien Tak Li, Fontenay aux Roses (FR); Aya Shoda, Tokyo (JP); Jonathan Reid Frost, Wissous (FR); Kazutoshi Watanabe, Tokyo (JP)

(73) Assignees: Sanofi-Synthelabo, Paris (FR); Mitsubishi Pharma Corporation, Tokyo (JP)

( * ) Notice: Subject to any disclaimer, the term of this patent is extended or adjusted under 35 U.S.C. 154(b) by 68 days.

(21) Appl. No.: 10/221,598

(22) PCT Filed: Mar. 22, 2001

(86) PCT No.: PCT/EP01/03640

§ 371 (c)(1),
(2), (4) Date: Dec. 2, 2002

(87) PCT Pub. No.: WO01/70729

PCT Pub. Date: Sep. 27, 2001

(65) Prior Publication Data

US 2003/0187004 A1 Oct. 2, 2003

(30) Foreign Application Priority Data

Mar. 23, 2000 (EP) .............................. 00400800

(51) Int. Cl.[7] ...................... C07D 401/04; A61K 31/505
(52) U.S. Cl. ................. 514/211.15; 514/218; 514/272; 514/273; 540/544; 540/575; 544/320; 544/321
(58) Field of Search ............................... 544/320, 321; 540/544, 575; 514/211.15, 218, 272, 273

(56) References Cited

U.S. PATENT DOCUMENTS 4,460,589 A    7/1984   Wierenga et al. ........... 424/251

FOREIGN PATENT DOCUMENTS

| JP | 07 435631 A | | 9/1974 |
| JP | 07 435633 A | | 9/1974 |
| JP | 49-035631 | * | 9/1974 |
| WO | WO 98 24780 A | | 6/1998 |
| WO | WO 00 18758 A | | 4/2000 |

OTHER PUBLICATIONS

Julien et al., PubMed Abstract (Prog Nucleic Acid Res Mol Biol. 61:1–23), 1998.*
Liu et al., PubMed Abstract (J Neurochem 87(6):1333–44), Dec. 2003.*
Damasio, Alzheimer's Disease and Related Dementias, Cecil Textbook of Medicine, 20th Edition, vol. 2, pp. 1992–1996, 1996.*
Layzer, Degenerative Diseases of the Nervous System, Cecil Textbook of Medicine, 20th Edition, vol. 2, pp. 2050–2057, 1996.*
Simone, Oncology: Introduction, Cecil Textbook of Medicine, 20th Edition, vol. 1, pp. 1004–1010, 1996.*
Chemical Abstracts, vol. 84, No. 7, Feb. 16, 1976, Columbus, OH, p. 502, Abstract No. 44112b.
Chemical Abstracts, vol. 83, No. 1, Jul. 7, 1975, Columbus, OH, p. 853, Abstract No. 10127z.

(List continued on next page.)

Primary Examiner—Deepak Rao
(74) Attorney, Agent, or Firm—Paul E. Dupont; Michael D. Alexander

(57) ABSTRACT

A pyrimidone derivative represented by formula (I) or a salt thereof:

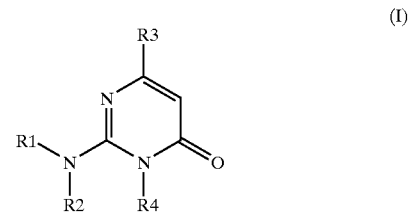

(I)

Wherein:
R1 represents a hydrogen atom or a $C_{1-6}$ alkyl group which may be substituted by a $C_{6,10}$ aryl group;
R2 represents a $C_{1-10}$ alkyl group which may be substituted, a $C_{2-6}$ alkenyl group which may be substituted, a $C_{3-6}$ alkynyl group which may be substituted, a $C_{3-6}$ cycloalkyl group which may be substituted, or a $C_{6-10}$ ARYL group which may be substituted;
or R1 and R2 form together a $C_{2-6}$ alkylene group which may be substituted;
or R1 and R2 form together a chain of formula —$(CH_2)_2$—X—$(CH_2)_2$— or —$(CH_2)_2$—X—$(CH_2)_3$— where X represents a oxygen atom, a sulfur atom, or a nitrogen atom which may be substituted;
R3 represents a 2, 3 or 4-pyridyl group optionally substituted by a $C_{1-4}$ alkyl group, $C_{1-4}$ alkoxy group or halogen atom; and
R4 represents a $C_{1-10}$ alkyl group optionally substituted by a hydroxyl group, amino, $C_{1-6}$ monoalkylamino group, $C_{2-12}$ dialkylamino group or $C_{6,10}$ aryl group which may be substituted.

And a medicament comprising the said derivative or a salt thereof as an active ingredient which is used for preventive and/or therapeutic treatment of a neurodegenerative disease caused by abnormal activity of GSK3β such as Alzheimer's disease.

4 Claims, No Drawings

OTHER PUBLICATIONS

H.I. Skulnick, et al.; "Pyrimidinones.3.N–Substituted 6–Phenylpyrimidinones and Pyrimidinediones with Diuretic/Hypotensive and Antiinflammatory Activity"; J. Med. Chem., vol. 29, No. 8, 1986, pp 1499–1504.

H.I. Skulnick, et al.; "Pyrimidinones.1.2 Amino–5–halo–6–aryl–4(3H)–pyrimidinones. Interferon–Inducing Antiviral Agents"; J. Med. Chem., vol. 28, No. 12, 1985, pp 1864–1869.

H.J. Kabbe; "Substituierte 4–Hydroxy–und 4–Amino–pyrimidine"; Liebigs Ann. Chem.; vol. 704; 1967; pp 144–149.

* cited by examiner

2-AMINO-3-(ALKYL)-PYRIMIDONE DERIVATIVES AS GSK3.β.INHIBITORS

TECHNICAL FIELD

The present invention relates to compounds that are useful as an active ingredient of a medicament for preventive and/or therapeutic treatment of neurodegenerative diseases caused by abnormal activity of GSK3β.

BACKGROUND ART

GSK3β (glycogen synthase kinase 3β) is a proline directed serine, threonine kinase that plays an important role in the control of metabolism, differentiation and survival. It was initially identified as an enzyme able to phosphorylate and hence inhibit glycogen synthase. It was later recognized that GSK3β was identical to tau protein kinase 1 (TPK1), an enzyme that phosphorylates tau protein in epitopes that are also found to be hyperphosphorylated in Alzheimer's disease and in several taupathies.

Interestingly, protein kinase B (AKT) phosphorylation of GSK3β results in a loss of its kinase activity, and it has been hypothesized that this inhibition may mediate some of the effects of neurotrophic factors. Moreover, phosphorylation by GSK3β of β-catenin, a protein involved in cell survival, results in its degradation by an ubiquitinilation dependent proteasome pathway.

Thus, it appears that inhibition of GSK3β activity may result in neurotrophic activity. Indeed there is evidence that lithium, an uncompetitive inhibitor of GSK3β, enhances neuritogenesis in some models and also increases neuronal survival, through the induction of survival factors such as Bcl-2 and the inhibition of the expression of proapoptotic factors such as P53 and Bax.

Recent studies have demonstrated that β-amyloid increases the GSK3β activity and tau protein phosphorylation. Moreover, this hyperphosphorylation as well as the neurotoxic effects of β-amyloid are blocked by lithium chloride and by a GSK3β antisense mRNA. These observations strongly suggest that GSK3β may be the link between the two major pathological processes in Alzheimer's disease: abnormal APP (Amyloid Precursor Protein) processing and tau protein hyperphosphorylation.

Although tau hyperphosphorylation results in a destabilization of the neuronal cytoskeleton, the pathological consequences of abnormal GSK3β activity are, most likely, not only due to a pathological phosphorylation of tau protein because, as mentioned above, an excessive activity of this kinase may affect survival through the modulation of the expression of apoptotic and antiapoptotic factors. Moreover, it has been shown that β-amyloid-induced increase in GSK3β activity results in the phosphorylation and, hence the inhibition of pyruvate dehydrogenase, a pivotal enzyme in energy production and acetylcholine synthesis.

Altogether these experimental observations indicate that GSK3β may find application in the treatment of the neuropathological consequences and the cognitive and attention deficits associated with Alzheimer's disease, as well as other acute and chronic neurodegenerative diseases. These include, in a non-limiting manner, Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma.

In addition GSK3β may find application in the treatment of other diseases such as: Non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

DISCLOSURE OF THE INVENTION

An object of the present invention is to provide compounds useful as an active ingredient of a medicament for preventive and/or therapeutic treatment of neurodegenerative diseases. More specifically, the object is to provide novel compounds useful as an active ingredient of a medicament that enables prevention and/or treatment of the diseases such as Alzheimer's.

Thus the inventors of the present invention have identified compounds possessing inhibitory activity against GSK3β.

As a result, they found that compounds represented by the following formula (I) had the desired activity and were useful as an active ingredient of a medicament for preventive and/or therapeutic treatment of the aforementioned diseases.

The present invention thus provides pyrimidone derivatives represented by formula (I) or salts thereof, solvates thereof or hydrates thereof:

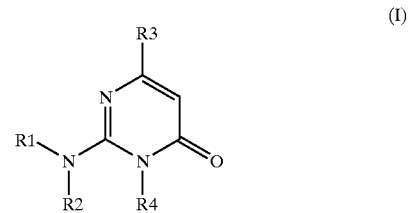

(I)

Wherein:

R1 represents a hydrogen atom or a $C_{1-6}$ alkyl group which may be substituted by a $C_{6,10}$ aryl group;

R2 represents a $C_{1-10}$ alkyl group which may be substituted, a $C_{2-6}$ alkenyl group which may be substituted, a $C_{3-6}$ alkynyl group which may be substituted, a $C_{3-6}$ cycloalkyl group which may be substituted, or a $C_{6-10}$ ARYL group which may be substituted;

or R1 and R2 form together a $C_{2-6}$ alkylene group which may be substituted;

or R1 and R2 form together a chain of formula —$(CH_2)_2$—X—$(CH_2)_2$— or —$(CH_2)_2$—X—$(CH_2)_3$— where X represents a oxygen atom, a sulfur atom, or a nitrogen atom which may be substituted;

R3 represents a 2, 3 or 4-pyridyl group optionally substituted by a $C_{1-4}$ alkyl group, $C_{1-4}$ alkoxy group or halogen atom; and R4 represents a $C_{1-10}$ alkyl group optionally substituted by a hydroxyl group, amino, $C_{1-6}$ monoalkylamino group, $C_{2-12}$ dialkylamino group or $C_{6,10}$ aryl group which may be substituted.

According to another aspect of the present invention, there is provided a medicament comprising as an active ingredient a substance selected from the group consisting of the pyrimidone derivatives represented by formula (I) and the physiologically acceptable salts thereof, and the solvates thereof and the hydrates thereof. As preferred embodiments of the medicament, there are provided the aforementioned medicament which is used for preventive and/or therapeutic treatment of diseases caused by abnormal GSK3β activity, and the aforementioned medicament which is used for preventive and/or therapeutic treatment of neurodegenerative diseases and in addition other diseases such as: Non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

As further preferred embodiments of the present invention, there are provided the aforementioned medicament wherein the diseases are neurodegenerative diseases and are selected from the group consisting of Alzheimer's disease, Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma, and the aforementioned medicament in the form of pharmaceutical composition containing the above substance as an active ingredient together with one or more pharmaceutical additives.

The present invention further provides an inhibitor of GSK3β activity comprising as an active ingredient a substance selected from the group consisting of the pyrimidone derivatives of formula (I) and the salts thereof, and the solvates thereof and the hydrates thereof.

According to further aspects of the present invention, there are provided a method for preventive and/or therapeutic treatment of neurodegenerative diseases caused by abnormal GSK3β activity, which comprises the step of administering to a patient a preventively and/or therapeutically effective amount of a substance selected from the group consisting of the pyrimidone derivatives of formula (I) and the physiologically acceptable salts thereof, and the solvates thereof and the hydrates thereof; and a use of a substance selected from the group consisting of the pyrimidone derivatives of formula (I) and the physiologically acceptable salts thereof, and the solvates thereof and the hydrates thereof for the manufacture of the aforementioned medicament.

As used herein, the $C_{1-6}$ alkyl group represents a straight or branched alkyl group having 1 to 6 carbon atoms, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, and the like;

The $C_{1-10}$ alkyl group represents a straight or branched alkyl group having 1 to 10 carbon atoms, for example in addition to the $C_{1-6}$ alkyl groups cited above, heptyl group, octyl group, nonyl group, decyl group, and the like;

The $C_{2-6}$ alkylene group represents a divalent alkyl group;

The $C_{2-6}$ alkenyl group represents an alkyl group having 2 to 6 carbon atoms and one or two double bond;

The $C_{3-6}$ alkynyl group represents an alkyl group having 3 to 6 carbon atoms and one or two triple bond;

The $C_{1-6}$ alkoxy group represents an alkyloxy group having 1 to 6 carbon atoms for example, methoxy group, ethoxy group, propoxy group, isopropoxy group, butoxy group, isobutoxy group, sec-butoxy group, tert-butoxy group, pentyloxy group, isopentyloxy group, neopentyloxy group, 1,1-dimethylpropyloxy group and the like;

The $C_{1-6}$ acyloxy group represents an alkylcarbonyloxy group having 1 to 6 carbon atoms for example, methylcarbonyloxy group, ethylcarbonyloxy group, propylcarbonyloxy group, isopropylcarbonyloxy group, butylcarbonyloxy group, isobutylcarbonyloxy group, sec-butylcarbonyloxy group, tert-butylcarbonyloxy group, pentylcarbonyloxy group, isopentylcarbonyloxy group, neopentylcarbonyloxy group, 1,1-dimethylpropylcarbonyloxy group and the like;

The halogen atom represents a fluorine, chlorine, bromine or iodine atom;

The $C_{1-2}$ perhalogenated alkyl group represents an alkyl group wherein all the hydrogen have been substituted by a halogen atom, for example a $CF_3$ or $C_2F_5$;

The $C_{1-3}$ halogenated alkyl group represents an alkyl group wherein at least one hydrogen has not been substituted by a halogen atom;

The $C_{6,10}$ aryl group represents a phenyl group, a naphth-1-yl group or a naphth-2-yl group;

The $C_{6-10}$ ARYL group for R2 represents an indan-1-yl ring, an indan-2-yl ring tetrahydronaphthalen-1-yl ring, tetrahydronaphthalen-2-yl ring, a phenyl group, naphth-1-yl group or a naphth-2-yl group;

The $C_{6,10}$ aryloxy group represents a phenoxy group, a 1-naphthyloxy group or a 2-naphthyloxy group;

The $C_{1-6}$ monoalkylamino group represents an amino group substituted by one $C_{1-6}$ alky group, for example, methylamino group, ethylamino group, propylamino group, isopropylamino group, butylamino group, isobutylamino group, tert-butylamino group, pentylamino group and isopentylamino group;

The $C_{2-12}$ dialkylamino group represents an amino group substituted by two $C_{1-6}$ alkyl groups, for example, dimethylamino group, ethylmethylamino group, diethylamino group, methylpropylamino group and diisopropylamino group;

The heterocyclic ring having 1–4 hetero atoms selected from oxygen atom, sulfur atom, and nitrogen atom, and having total ring-constituting atoms of 5–10 represents, for example, a furan ring, dihydrofuran ring, tetrahydrofuran ring, pyran ring, dihydropyran ring, tetrahydropyran ring, benzofuran ring, furopyridine ring, isobenzofuran ring, chromene ring, chroman ring, isochroman ring, thiophene ring, benzothiophene ring, thienopyridine ring, pyrrole ring, pyrroline ring, pyrrolidine ring, imidazole ring, imidazoline ring, imidazolidine ring, imidazopyridine ring, pyrazole ring, pyrazoline ring, pyrazolidine ring, triazole ring, tetrazole ring, pyridine ring, pyridine oxide ring, piperidine ring, pyrazine ring, piperazine ring, pyrimidine ring, pyridazine ring, indolizine ring, indole ring, indoline ring, isoindole ring, isoindoline ring, indazole ring, benzimidazole ring, purine ring, quinolizine ring, quinoline ring, isoquinoline ring, phthalazine ring, naphtyridine ring, quinoxaline ring, quinazoline ring, cinnoline ring, pteridine ring, oxazole ring, oxazolidine ring, isoxazole ring, isoxazolidine ring, thiazole ring, benzothiazole ring, thiazylidine ring, isothiazole ring, isothiazolidine ring, dioxane ring, dithian ring, morpholine ring, thiomorpholine ring, phthalimide ring, tetrahydropyridoindole ring, tetrahydroisoquinoline ring, tetrahydrothienopyridine ring, tetrahydrobenzofuropyridine ring, and the like.

When R2 represents a $C_{1-10}$ alkyl group, a $C_{2-6}$ alkenyl group, a $C_{3-6}$ alkynyl, a $C_{3-6}$ cycloalkyl group which may be substituted, these groups may have 1 or 3 substituents selected form the group consisting of a $C_{3-6}$ cycloalkyl, an adamantyl, a $C_{3-6}$ cycloalkyloxy group, a $C_{1-6}$ alkoxy group, a $C_{6,10}$ aryloxy group which may be substituted, a hydroxyl group, a $C_{1-6}$ alkylthio group, a $C_{6,10}$ arylthio group, an amino, a $C_{1-6}$ monoalkylamino group, a $C_{2-12}$ dialkylamino group, a $C_{6,10}$ arylamino group, a $C_{1-6}$ acyloxy, a $C_{6,10}$ aryl group which may be substituted, a heterocyclic ring having 1–4 hetero atoms selected from oxygen atom, sulfur atom, and nitrogen atom, and having total ring-constituting atoms of 5–10 which may be substituted.

When a $C_{6,10}$ aryl group may be substituted, the $C_{6,10}$ aryl group may have 1 to 3 substituents selected from the group consisting of a $C_{1-6}$ alkyl group, halogen atom, a $C_{1-2}$ perhalogenated alkyl group, a $C_{1-3}$ halogenated alkyl group, a hydroxyl group, a $C_{1-6}$ alkoxy group, methylenedioxy group, a nitro, a cyano, an amino, a $C_{1-6}$ monoalkylamino group, a $C_{2-12}$ dialkylamino group, a ($C_{1-6}$-alkyl)carbonylamino group, a ($C_{6,10}$-aryl)carbonylamino group, a ($C_{1-6}$-alkoxy)carbonylamino group, aminocarbonyl group, a ($C_{1-6}$-monoalkylamino)carbonyl group, a ($C_{2-12}$-dialkylamino)carbonyl group, a formyl, a $C_{1-6}$ alkylcarbonyl group, a ($C_{6,10}$-aryl)carbonyl group, a $C_{1-6}$ alkylsulfonyl group, a $C_{6,10}$ arylsulfonyl group, aminosulfonyl group, a $C_{1-6}$ monoalkylaminosulfonyl group, a $C_{2-12}$ dialkylaminosulfonyl group, or a phenyl group;

Wherein the $C_{1-6}$ alkyl groups and the $C_{1-6}$ alkoxy groups are optionally substituted by a halogen atom, a hydroxyl group, a $C_{1-6}$ alkoxy group, a $C_{1-6}$ acyloxy group, an amino, a $C_{1-6}$ monoalkylamino group, a $C_{2-12}$ dialkylamino group, a ($C_{1-6}$-alkyl)carbonylamino group, an amino-$C_{1-6}$ alkyl, a $C_{1-6}$ monoalkylamino-$C_{1-6}$ alkyl group, a $C_{2-12}$ dialkylamino-$C_{1-6}$ alkyl group, a ($C_{1-6}$-alkyl)carbonylamino group a ($C_{6,10}$-aryl)carbonylamino group, a ($C_{1-6}$-alkoxy) carbonylamino group, a $C_{1-6}$ alkylsulfonylamino group, a $C_{6,10}$ arylsulfonylamino group, a phenyl group or a heterocyclic ring having 1–4 hetero atoms selected from oxygen atom, sulfur atom, and nitrogen atom, and having total ring-constituting atoms of 5–10 which may be substituted.

When a $C_{6-10}$ ARYL group may be substituted, the $C_{6-10}$ ARYL group may have 1 to 3 substituents selected from the group consisting of a $C_{1-6}$ alkyl group, halogen atom, a $C_{1-2}$ perhalogenated alkyl group, a $C_{1-3}$ halogenated alkyl group, a hydroxyl group, a $C_{1-6}$ alkoxy group, methylenedioxy group, a nitro, a cyano, an amino, a $C_{1-6}$ monoalkylamino group, a $C_{2-12}$ dialkylamino group, a ($C_{1-6}$ alkyl) carbonylamino group, a ($C_{6,10}$ aryl)carbonylamino group, a ($C_{1-6}$ alkoxy)carbonylamino group.

When a $C_{6,10}$ aryloxy group may be substituted, the $C_{6,10}$ aryl group may have 1 to 3 substituents as defined above for the $C_{6,10}$ aryl group.

When the heterocyclic ring having 1–4 hetero atoms selected from oxygen atom, sulfur atom, and nitrogen atom, and having a total ring-constituting atoms of 5–10, may be substituted, the heterocyclic ring may have 1 to 3 substituents selected from the group consisting of a $C_{1-6}$ alkyl group, halogen atom, a $C_{1-2}$ perhalogenated alkyl group, a $C_{1-3}$ halogenated alkyl group, a hydroxyl group, a $C_{1-6}$ alkoxy group, a nitro, a cyano, an amino, a $C_{1-6}$ monoalkylamino group, a $C_{2-12}$ dialkylamino group, a ($C_{1-6}$-alkyl)carbonylamino group, a ($C_{6,10}$ aryl)carbonylamino group, a ($C_{1-6}$ alkoxy)carbonylamino group, aminocarbonyl group, a ($C_{1-6}$ monoalkylamino)carbonyl group, a ($C_{2-12}$ dialkylamino)carbonyl group, a formyl, a $C_{1-6}$ alkylcarbonyl group, a ($C_{6,10}$ aryl)carbonyl group, a $C_{1-6}$ alkylsulfonyl group, a $C_{6,10}$ arylsulfonyl group, aminosulfonyl group, a $C_{1-6}$ monoalkylaminosulfonyl group, a $C_{2-12}$ dialkylaminosulfonyl group, or a phenyl group;

Wherein the $C_{1-6}$ alkyl groups and the $C_{1-6}$ alkoxy group being optionally substituted by a halogen atom, a hydroxyl group, a $C_{1-6}$ alkoxy group, an amino, a $C_{1-6}$ monoalkylamino group, a $C_{2-12}$ dialkylamino group, a ($C_{1-6}$ alkyl)carbonylamino group, a ($C_{6,10}$ aryl) carbonylamino group, a ($C_{1-6}$ alkoxy)carbonylamino group, a $C_{1-6}$ alkylsulfonylamino group, a $C_{6,10}$ arylsulfonylamino group or a phenyl group.

When the $C_{2-6}$ alkylene group may be substituted, the $C_{2-6}$ alkylene group may have 1 to 3 substituents selected from a group consisting of a $C_{1-6}$ alkyl group which may be substituted by a $C_{6,10}$ aryl group which may be substituted, a $C_{1-6}$ alkyl group which may be substituted by a heterocyclic ring which may be substituted, a $C_{6,10}$ aryl group which may be substituted, a heterocyclic ring which may be substituted; the substituents being as defined here above.

When R1 and R2 form together a chain of formula —(CH$_2$)$_2$—X—(CH$_2$)$_2$— or —(CH$_2$)$_2$—X—(CH$_2$)$_3$— wherein X represents a nitrogen atom which may be substituted, the group NR1R2 represents a piperazine ring or homopiperazine which may be substituted in position 4 by a substituent selected from the group consisting of a $C_{1-6}$ alkyl group which may be substituted by a $C_{6,10}$ aryl group which may be substituted or by a heterocyclic ring which may be substituted; a $C_{6,10}$ aryl group which may be substituted or a heterocyclic ring which may be substituted, the substituents being as defined hereabove.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, and L-glucamine; or salts with basic amino acids such as lysine, δ-hydroxylysine, and arginine. The base-addition salts of acidic compounds are prepared by standard procedures well known in the art.

When a basic group exists, examples include salts with mineral acids such as hydrochloric acid, hydrobromic acid, sulfuric acid, nitric acid, phosphoric acid; salts with organic acids such as methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, and salicylic acid; or salts with acidic amino acids such as aspartic acid, and glutamic acid.

The acid-addition salts of the basic compounds are prepared by standard procedures well know in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not compromised by side effects ascribable to the anions. Although medicinally acceptable salts of the basic compounds are preferred, all acid-addition salts are within the scope of the present invention.

In addition to the pyrimidone derivatives represented by the aforementioned formula (I) and salts thereof, their solvates and hydrates also fall within the scope of the present invention. The pyrimidone derivatives represented by the aforementioned formula (I) may have one or more asymmetric carbon atoms. As for the stereochemistry of such asymmetric carbon atoms, they may independently be in either (R) and (S) configuration, and the pyrimidone derivative may exist as stereoisomers such as optical isomers, or diastereoisomers. Any stereoisomers in pure form, any mixtures of stereoisomers, racemates and the like fall within the scope of the present invention.

Examples of preferred compounds of the present invention are shown in table 1 hereinafter. However, the scope of the present invention is not limited by these compounds.

Preferred compounds of the present invention represented by formula (I) include also:

(1) Compounds wherein R3 represents a 3- or4-pyridyl group and more preferably 4-pyridyl group which may be substituted by a $C_{1-2}$ alkyl group, $C_{1-2}$ alkoxy group or halogen atom;
(2) Compounds wherein R1 represents a hydrogen atom or a $C_{1-3}$ alkyl group which may be substituted by a phenyl group;
(3) Compounds wherein R2 represents an unsubstituted $C_{1-10}$ alkyl group;
(4) Compounds wherein R2 represents a substituted $C_{1-6}$ alkyl group, a $C_{3-6}$ cycloalkyl group which may be substituted, an indanyl group which may be substituted or a $C_{2-4}$ alkenyl group which may be substituted;
(5) Compounds wherein R1 represents a hydrogen atom or a $C_{1-3}$ alkyl group and R2 represents a $C_{1-6}$ alkyl group which may be substituted, a $C_{3-6}$ cycloalkyl group which may be substituted, an indanyl group which may be substituted;
(6) Compounds wherein R1 and R2 form together a $C_{2-6}$ alkylene group.

More preferred compounds of the present invention represented by formula (I) include also:

(1) Compounds wherein R3 represents an unsubstituted 4-pyridyl group;
(2) Compounds wherein R1 represents a hydrogen atom or a $C_{1-3}$ alkyl group which may be substituted by a phenyl group and R2 represents a $C_{1-6}$ alkyl group which may be substituted by a $C_{3-6}$ cycloalkyl, an adamantyl, a $C_{1-6}$ alkoxy group, a hydroxyl group, a phenylthio group, an amino, a $C_{1-6}$ monoalkylamino group, a $C_{2-12}$ dialkylamino group, a phenylamino group, a $C_{1-6}$ acyloxy, a phenyl group which may be substituted, a heterocyclic ring having 1–4 hetero atoms selected from oxygen atom, sulfur atom, and nitrogen atom, and having total ring-constituting atoms of 5–10 which may be substituted, preferably the heterocyclic ring being selected from an indole ring or a substituted indole ring, a thiophene or substituted thiophene ring, a pyridine ring and a piperidine ring;
(3) Compounds wherein R3 is defined as specified under (1), and R1 and R2 are specified under (2) for the more preferred compounds;
(4) Compounds wherein R1 represents a hydrogen atom or a $C_{1-3}$ alkyl group and R2 represents an indanyl group or an substituted indanyl group.

Particularly preferred compounds of the present invention represented by formula (I) include:

2-[[2-(phenyl)ethyl]amino]-3-methyl-6-pyridin-4-ylpyrimidin-4(3H)-one,
2-[[2-(4-methoxyphenyl)ethyl]amino]-3-methyl-6-pyridin-4-ylpyrimidin-4(3H)-one,
2-[[2-(3-methoxyphenyl)ethyl]amino]-3-methyl-6-pyridin-4-ylpyrimidin-4(3H)-one,
2-[[2-(2-methoxyphenyl)ethyl]amino]-3-methyl-6-pyridin-4-ylpyrimidin-4(3H)-one,
2-[[2-(2-fluorophenyl)ethyl]amino]-3-methyl-6-pyridin-4-ylpyrimidin-4(3H)-one,
2-[[2-(3-fluorophenyl)ethyl]amino]-3-methyl-6-pyridin-4-ylpyrimidin-4(3H)-one,
2-[[2-(4-fluorophenyl)ethyl]amino]-3-methyl-6-pyridin-4-ylpyrimidin-4(3H)-one,
2-[[2-(4-bromophenyl)ethyl]amino]-3-methyl-6-pyridin-4-ylpyrimidin-4(3H)-one,
2-[[2-(2-chlorophenyl)ethyl]amino]-3-methyl-6-pyridin-4-ylpyrimidin-4(3H)-one,
2-[[2-(2,4-dichlorophenyl)ethyl]amino]-3-methyl-6-pyridin-4-ylpyrimidin-4(3H)-one,
2-[[2-(4-aminophenyl)ethyl]amino]-3-methyl-6-pyridin-4-ylpyrimidin-4(3H)-one,
2-[[2-(3,4-dimethoxyphenyl)ethyl]amino]-3-methyl-6-pyridin-4-ylpyrimidin-4(3H)-one,
2-[[2-(2,5-dimethoxyphenyl)ethyl]amino]-3-methyl-6-pyridin-4-ylpyrimidin-4(3H)-one,
2-[[2-(4-chlorophenyl)ethyl]amino]-3-methyl-6-pyridin-4-ylpyrimidin-4(3H)-one,
2-[[2-(4-hydroxyphenyl)ethyl]amino]-3-methyl-6-pyridin-4-ylpyrimidin-4(3H)-one,
2-[[2-(4-methylphenyl)ethyl]amino]-3-methyl-6-pyridin-4-ylpyrimidin-4(3H)-one
2-[[2-(4-aminosulfonylphenyl)ethyl]amino]-3-methyl-6-pyridin-4-ylpyrimidin-4(3H)-one,
2-[[2-(3-chlorophenyl)ethyl]amino]-3-methyl-6-pyridin-4-ylpyrimidin-4(3H)-one,
2-[[2-(thiophen-2-yl)ethyl]amino]-3-methyl-6-pyridin-4-ylpyrimidin-4(3H)-one,
2-[[4-(phenyl)butyl]amino]-3-methyl-6-pyridin-4-ylpyrimidin-4(3H)-one,
2-[[2-(4-phenylmethoxyphenyl)ethyl]amino]-3-methyl-6-pyridin-4-ylpyrimidin-4(3H)-one,
2-[[2-(4-phenylphenyl)ethyl]amino]-3-methyl-6-pyridin-4-ylpyrimidin-4(3H)-one,
2-[(phenylmethyl)amino]-3-methyl-6-pyridin-4-ylpyrimidin-4(3H)-one,
2-[[(2-methoxyphenyl)methyl]amino]-3-methyl-6-pyridin-4-ylpyrimidin-4(3H)-one,
2-[[2-(2,5-dimethoxyphenyl)ethyl]methylamino]-3-methyl-6-pyridin-4-ylpyrimidin-4(3H)-one,
2-[[[3-(3-aminopropoxy)phenyl]methyl]amino]-3-methyl-6-pyridin-4-ylpyrimidin-4(3H)-one,
2-[[[3-(aminomethyl)phenyl]methyl]amino]-3-methyl-6-pyridin-4-ylpyrimidin-4(3H)-one,
2-[[3-(phenyl)propyl]amino]-3-phenylmethyl-6-pyridin-4-ylpyrimidin-4(3H)-one,
2-[[2-(1H-indol-3-yl)ethyl]amino]-3-methyl-6-pyridin-4-yl pyrimidin-4(3H)-one,
2-[[2-(5-methoxy-1H-indol-3-yl)ethyl]amino]-3-methyl-6-pyridin-4-yl pyrimidin-4(3H)-one,
2-[[2-(5-phenylmethoxy-1H-indol-3-yl)ethyl]amino]-3-methyl-6-pyridin-4-yl pyrimidin-4(3H)-one, 2-[[2-(7-methyl-1H-indol-3-yl)ethyl]amino]-3-methyl-6-pyridin-4-yl pyrimidin-4(3H)-one,
2-[[2-(1-methyl-1H-indol-3-yl)ethyl]amino]-3-methyl-6-pyridin-4-yl pyrimidin-4(3H)-one,
2-[[2-(1-methyl-1H-indol-3-yl)ethyl]methylamino]-3-methyl-6-pyridin-4-ylpyrimidin-4(3H)-one,
2-(cyclopentylamino)-3-methyl-6-pyridin-4-ylpyrimidin-4(3H)-one,
2-(ethylamino)-3-methyl-6-pyridin-4-ylpyrimidin-4(3H)-one,
2-[(indan-2-yl)amino]-3-methyl-6-pyridin-4-ylpyrimidin-4(3H)-one,
2-(piperidin-1-yl)-3-methyl-6-pyridin-4-ylpyrimidin-4(3H)-one,
2-(pyrrolidin-1-yl)-3-methyl-6-pyridin-4-ylpyrimidin-4(3H)-one,
2-(5-Amino-pentylamino)-3-methyl-6-pyridin-4-yl-3H-pyrimidin-4-one,
2-(4-Amino-butylamino)-3-(3-phenyl-propyl)-6-pyridin-4-yl-3H-pyrimidin-4-one,
2-(6-Amino-hexylamino)-3-(3-phenyl-propyl)-6-pyridin-4-yl-3H-pyrimidin-4-one,
2-(5-Amino-pentylamino)-3-phenethyl-6-pyridin-4-yl-3H-pyrimidin-4-one,
2-(6-Amino-hexylamino)-3-phenethyl-6-pyridin-4-yl-3H-pyrimidin-4-one,
2-(4-Amino-butylamino)-3-phenethyl-6-pyridin-4-yl-3H-pyrimidin-4-one,
2-Cyclohexylamino-3-methyl-6-pyridin-4-yl-3H-pyrimidin-4-one,
2-Butylamino-3-methyl-6-pyridin-4-yl-3H-pyrimidin-4-one,
3-Methyl-2-pentylamino-6-pyridin-4-yl-3H-pyrimidin-4-one,
2-Hexylamino-3-methyl-6-pyridin-4-yl-3H-pyrimidin-4-one,
2-Heptylamino-3-methyl-6-pyridin-4-yl-3H-pyrimidin-4-one,
3-Methyl-2-octylamino-6-pyridin-4-yl-3H-pyrimidin-4-one,
3-Methyl-2-nonylamino-6-pyridin-4-yl-3H-pyrimidin-4-one,
2-Decylamino-3-methyl-6-pyridin-4-yl-3H-pyrimidin-4-one,
2-(2-Cyclohexyl-ethylamino)-3-methyl-6-pyridin-4-yl-3H-pyrimidin-4-one,
3-Methyl-2-(3-methyl-butylamino)-6-pyridin-4-yl-3H-pyrimidin-4-one,
2-(Cyclohexylmethyl-amino)-3-methyl-6-pyridin-4-yl-3H-pyrimidin-4-one,
3-Methyl-2-(2-propoxy-ethylamino)-6-pyridin-4-yl-3H-pyrimidin-4-one,
2-(3-Cyclohexyl-propylamino)-3-methyl-6-pyridin-4-yl-3H-pyrimidin-4-one,
2-(3-Ethoxy-propylamino)-3-methyl-6-pyridin-4-yl-3H-pyrimidin-4-one,
2-[(5-Amino-pentyl)-phenetyl-amino]-3-methyl-6-pyridin-4-yl-3H-pyrimidin-4-one,
2-(5-Hydroxy-pentylamino)-3-methyl-6-pyridin-4-yl-3H-pyrimidin-4-one,
2-(4-Hydroxy-butylamino)-3-methyl-6-pyridin-4-yl-3H-pyrimidin-4-one,
2-(3-Isopropoxy-propylamino)-3-methyl-6-pyridin-4-yl-3H-pyrimidin-4-one,
3-Methyl-2-(3-propoxy-propylamino)-6-pyridin-4-yl-3H-pyrimidin-4-one,
2-(2-Hydroxy-2-phenyl-ethylamino)-3-methyl-6-pyridin-4-yl-3H-pyrimidin-4-one,
2-(2-Cyclopentyl-ethylamino)-3-methyl-6-pyridin-4-yl-3H-pyrimidin-4-one,
3-Methyl-2-(3-piperidin-1-yl-propylamino)-6-pyridin-4-yl-3H-pyrimidin-4-one,
2-[(3-Cyclohexyl-propyl)-methyl-amino]-3-methyl-6-pyridin-4-yl-3H-pyrimidin-4-one,
Acetic acid 2-(1-methyl-6-oxo-4-pyridin-4-yl-1,6-dihydro-pyrimidin-2-ylamino)-1-phenyl-ethyl ester
2-(2-Adamnantan-1-yl-ethylamino)-3-methyl-6-pyridin-4-yl-3H-pyrimidin-4-one,
2-[3-(3-Hydroxy-propoxy)-benzylamino]-3-methyl-6-pyridin-4-yl-3H-pyrimidin-4-one,
3-methyl-2-[3-(2-piperidin-4-yl-ethoxy)-benzylamino]-6-pyridin-4-yl-3H-pyrimidin-4-one,
Acetic acid 3-{3-[(1-methyl-6-oxo-4-pyridin-4-yl-1,6-dihydro-pyrimidin-2-ylamino)-methyl]-phenoxy}-propyl ester
2-[3-(3-Dimethylamino-propoxy)-benzylamino]-3-methyl-6-pyridin-4-yl-3H-pyrimidin-4-one,
3-Methyl-2-{methyl-[2-(4-methylaminomethyl-phenyl)-ethyl]-amino}-6-pyridin-4-yl-3H-pyrimidin-4-one,
2-[(4-Amino-butyl)-phenethyl-amino]-3-methyl-6-pyridin-4-yl-3H-pyrimidin-4-one,
3-(3-Amino-propyl)-2-(3-phenyl-propylamino)-6-pyridin-4-yl-3H-pyrimidin-4-one,
3-Methyl-2-(3-phenyl-propylamino)-6-pyridin-4-yl-3H-pyrimidin-4-one,
3-(5-Amino-pentyl)-2-(3-phenyl-propylamino)-6-pyridin-4-yl-3H-pyrimidin-4-one,
3-(4-Amino-butyl)-2-(3-phenyl-propylamino)-6-pyridin-4-yl-3H-pyrimidin-4-one,
3-Methyl-6-pyridin-4-yl-2-[3-(3-pyridin-4-yl-propoxy)-benzylamino]-3H-pyrimidin-4-one,
3-(6-Amino-hexyl)-2-(3-phenyl-propylamino)-6-pyridin-4-yl-3H-pyrimidin-4-one,
3-(6-Amino-hexyl)-2-phenethylamino-6-pyridin-4-yl-3H-pyrimidin-4-one,
3-(2-Amino-ethyl)-2-(3-phenyl-propylamino)-6-pyridin-4-yl-3H-pyrimidin-4-one,
3-(3-Amino-propyl)-2-[2-(2-methoxy-phenyl)-ethylamino]-6-pyridin-4-yl-3H-pyrimidin-4-one,
3-(2-Hydroxy-ethyl)-2-(3-phenyl-propylamino)-6-pyridin-4-yl-3H-pyrimidin-4-one,
3-(2-Dimethylamino-ethyl)-2-(3-phenyl-propylamino)-6-pyridin-4-yl-3H-pyrimidin-4-one,
3-(5-Amino-pentyl)-2-phenethylamino-6-pyridin-4-yl-3H-pyrimidin-4-one,
3-(4-Amino-butyl)-2-phenethylamino-6-pyridin-4-yl-3H-pyrimidin-4-one,
2-(4-Amino-butylamino)-3-benzyl-6-pyridin-4-yl-3H-pyrimidin-4-one,
2-(6-Amino-hexylamino)-3-benzyl-6-pyridin-4-yl-3H-pyrimidin-4-one,
3-Methyl-2-(2-phenylthio-ethylamino)-6-pyridin-4-yl-3H-pyrimidin-4-one,
3-Methyl-2-(2-phenylamino-ethylamino)-6-pyridin-4-yl-3H-pyrimidin-4-one,
3-Methyl-2-(2-phenoxy-ethylamino)-6-pyridin-4-yl-3H-pyrimidin-4-one,
3-Methyl-2-(3-phenyl-allylamino)-6-pyridin-4-yl-3H-pyrimidin-4-one,
3-Methyl-2-(3-phenyl-propylamino)-6-pyridin-4-yl-3H-pyrimidin-4-one, and 3-Methyl-6-pyridin-4-yl-2(2-pyridin-2-yl-ethylamino)-3H-pyrimidin-4-one.

As a further object, the present invention concerns also methods for preparing the pyrimidone compounds represented by the aforementioned formula (I).

These compounds can be prepared, for example, according to the methods explained below.

1. Preparation Method 1

Pyrimidone compounds represented by the aforementioned formula (I) may be prepared according to scheme 1.

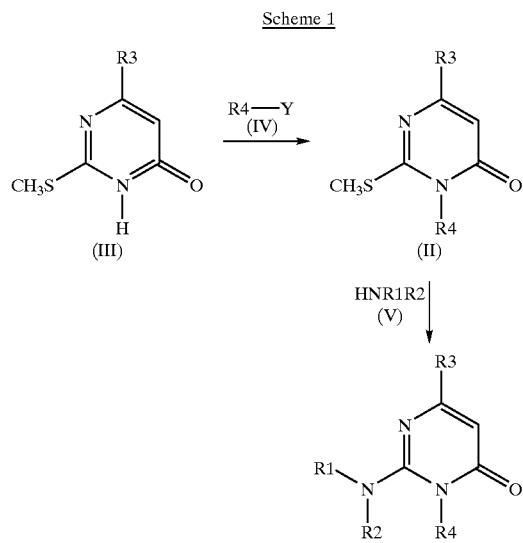

(In the above scheme the definition of R1, R2, R3 and R4 are the same as those already describe above for compounds of formula (I)).

The 2-methylthio derivative represented by the above formula (III), wherein R3 is as defined for compound of formula (I), is allowed to react with a compound of formula (IV), wherein Y represents a halogen atom such as for example a bromine or iodine in the presence of a base such as for example potassium carbonate, to obtain a compound of formula (II). The reaction may be carried out in aprotic polar solvents such as formamide, N,N-dimethylformamide, N,N-dimethylacetamide, N-methylpyrrolidone and the like, at a suitable temperature ranging from −10 to +20° C. under ordinary air.

Compound of formula (II) may then react with an amine of formula (V) to obtain the compound of the aforementioned formula (I). The reaction may be carried out in pyridine in presence of 1,8-diazabicyclo[5.4.0]undec-7-ene (DBU), at a suitable temperature ranging from 25° C. to reflux temperature.

Compound of formula (III) may be prepared according to the method defined in scheme 2.

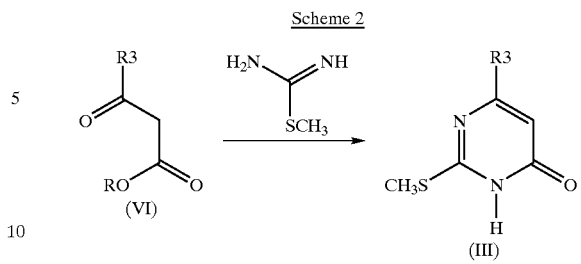

(In the above scheme R represents an alkyl group and the definition of R2 and R3 are the same as those already described for compound of formula (I).)

According to this method, the 3-ketoester of formula (VI) is allowed to react with a 2-methyl-2-thiopseudourea sulfate in the presence of a base such as potassium hydroxide. The reaction may be carried out in solvent such as water or an alcohol, such as ethanol, propanol and butanol, at a suitable temperature ranging from 25–100° C. under ordinary air.

Compounds of formula (IV), (V) and formula (VI) are commercially available or may be synthesized according to known methods of one skilled in the art.

For example compounds of formula (VI), wherein R, R2 and R3 are as defined above, can be prepared by reacting a nicotinic acid optionally substituted by a $C_{1-4}$ alkyl group, $C_{1-4}$ alkoxy group or an halogen, with a malonic acid monoester. The reaction can be carried out using methods well known to one skilled in the art, such as for example in presence of a coupling agent such as 1,1'-carbonylbis-1H-imidazole in a solvent such as a tetrahydrofuran at a temperature ranging from 20 to 70° C.

2. Preparation Method 2

Alternatively pyrimidone compounds represented by the aforementioned formula (I) may be prepared according to scheme 2.

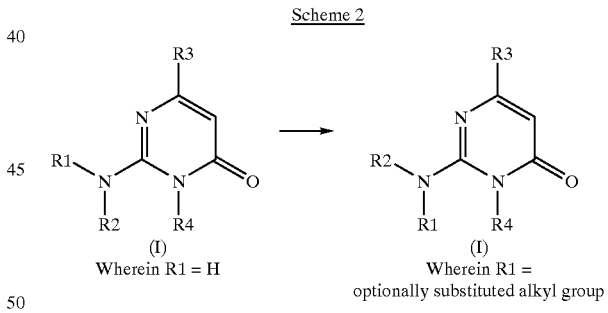

Compounds of formula (I) wherein R1 represents a hydrogen atom, can be alkylated by methods well known to one skilled in the art such as, for example, by reacting (I), wherein R1 represents a hydrogen atom, with sodium hydride, in an aprotic polar such as dimethylacetamide or dimethylformamide at a temperature ranging from 0° to 10°. An alkylating agent such as an optionally substituted $C_{1-6}$ alkyl halide is then added to obtain the compound of the above mentioned formula (I) wherein R1 represents an optionally substituted $C_{1-6}$ alkyl group.

In addition when applicable, compound of formula (I) can be derivatised affording other compounds of formula (I), using well known methods in the art, for example when the $C_{6,10}$ aryl groups or the heterocyclic ring is substituted by a hydroxyl group, the hydroxyl group can be alkylated to give a $C_{1-6}$ alkoxy group, or when the $C_{6-10}$ ARYL group, the $C_{6,10}$ aryl group or the heterocyclic ring is substituted by an amino group or an aminoalkyl group, the amino function can be alkylated, acylated, etc. . . . to give the corresponding derivatives.

In the above reactions, protection or deprotection of a functional group may sometimes be necessary. A suitable protecting group can be chosen depending on the type of a functional group, and a method described in the literature may be applied. Examples of protecting groups, of protection and deprotection methods are given for example in *Protective groups in Organic Synthesis* Greene et al., 2nd Ed. (John Wiley & Sons, Inc., New York).

The compounds of the present invention have inhibitory activity against GSK3β. Accordingly, the compounds of the present invention are useful as an active ingredient for the preparation of a medicament, which enables preventive and/or therapeutic treatment of neurodegenerative diseases such as Alzheimer's disease. In addition, the compounds of the present invention are also useful as an active ingredient for the preparation of a medicament for preventive and/or therapeutic treatment of neurodegenerative diseases such as Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma; and other diseases such as non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

The present invention further relates to a method for treating neurodegenerative diseases caused by abnormal activity of GSK3β and of the aforementioned diseases which comprises administering to a mammalian organism in need thereof an effective amount of a compound of the formula (I).

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more of pharmaceutical additives. As the active ingredient of the medicament of the present invention, two or more of the aforementioned substances may be used in combination. The above pharmaceutical composition may be supplemented with an active ingredient of another medicament for the treatment of the above mentioned diseases. A type of the pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

Dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

CHEMICAL EXAMPLES

The present invention will be explained more specifically with reference to the following general examples, however, the scope of the present invention is not limited to these examples.

EXAMPLE 1

Preparation of Substituted 2-amino-3-methylpyrimidinones (Method 1)

1.1. Preparation of Ethyl 3-(4-pyridyl)-3-oxopropionate

Isonicotinic acid (35.56 g, 289 mmol) was added to a solution of 1,1'-carbonylbis-1H-imidazole (46.98 g, 290 mmol) in tetrahydrofuran (700 ml), and the resulting solution was stirred for 1.5 hr at 50° C. After cooling to room temperature, malonic acid monoester potassium salt (51.7 g, 304 mmol) and magnesium chloride (34.33 g, 361 mmol) were added, and the mixture was refluxed for 1 hr and then heated at 50° C. for 6 hr. The solvent was removed under reduced pressure and the residue was quenched by the addition of dilute acetic acid. The organic layer was extracted with ethyl acetate (3 times) and the combined extracts were washed with dilute aqueous sodium bicarbonate and brine, and were concentrated under reduced pressure. The residue was purified by silica gel column chromatography (eluent; hexane/ethyl acetate=2/1 to 1/1) and recrystallization from hexane-ethyl acetate gave 41.52 g (74%) of the title compound.

1.2. Preparation of 2-(Methylthio)-6-pyridinyl-4-ylpyrimidin-4(1H)-one

To a solution of 5.76 g (20.7 mmol) of 2-methyl-2-thiopseudoiurea sulfate in 48 ml of water was added 4.85 g (86.52 mmol) of potassium hydroxide. The mixture was agitated and 8.0 g (41.4 mmol) of ethyl 3-(4-pyridyl)-3-oxopropionate was added and stirring was maintained for 48 hours.

The precipitate was recovered by filtration and was washed with water and then ether. The product was dried at 90° C. in vacuo to give 6.26 g, 69% of white solid.

Mp: 328–330° C.

1.3. Preparation of 3-methyl-2-(methylthio)-6-pyridin-4-yl-pyrimidin-4(3H)-one

To 3.0 g (13.7 mmol) of 2-methylthio-6-(4-pyridyl) pyrimidin-4-one in 50 ml of dimethylformamide was added 2.08 g (15.05 mmol) of potassium carbonate, followed by 0.85 ml (13.68 mmol) of methyl iodide at 0° C. and stirring was maintained for 1.5 hours.

The reaction mixture was added to cold water and extracted with dichloromethane. The solvent was evaporated and the resulting solid was purified by chromatography on silica gel, eluting with a mixture of dichloromethane/methanol (99:1 to 90:10) to give 2.36 g, 78% of a white solid.

Mp. 176–178° C.

1.4. Preparation of Substituted 2-amino-3-methylpyrimidinones

A solution of 1 equivalent of 3-methyl-2-(methylthio)-6-pyridin-4-yl-pyrimidin-(3H)-one and 1–5 equivalents of an amine of formula HNR4R5 were suspended in pyridine (0.1–1 M) containing 3 equivalents of the DBU (1,8-diazabicyclo[5.4.0]undec-7-ene) and was refluxed 24 hours.

The cooled solution was treated with a saturated aqueous solution of ammonium chloride and extracted with dichloromethane. The organic layer was dried and evaporated to give crude product which was purified by chromatography on silica gel.

2. Preparation of Substituted 2-alkylamino-3-alkylpyrimidinones (Method 2)

To a cooled (0° C.) solution of substituted 2-amino-3-methylpyrimidinone (1 equivalent, 0.1 mole) in N,N-dimethylacetamide (0.35 ml) was added sodium hydride (0.11 mmole). The mixture was stirred for 5 min and alkyl iodide (0.1 mmole) was added, stirred for further 20 min at 0° C. and the for 40 min at room temperature. Water (10 ml) was added, and the reaction mixture was extracted with ethyl acetate (3×3 ml). The organic phases was separated, dried over sodium sulfate and evaporated to afford a residue which was purified by chromatograpy on silica gel.

A list of chemical structures and physical data for compounds of the aforementioned formula (I) illustrating the present invention is given in table 1. The compounds have been prepared according to the examples.

Table 1: on following pages

In the table: Me represents a methyl group

Ph represents an phenyl group

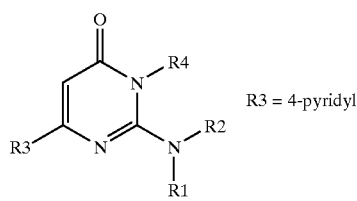

R3 = 4-pyridyl

| No. | R1 | R2 | R4 | m.p. (° C.) | [M + H]⁺ |
|---|---|---|---|---|---|
| 1 | H | -CH₂-C₆H₅ | Me | 186–187.5 | 307 |
| 2 | H | -CH₂-C₆H₄-OMe (para) | Me | 142.4–142.6 | 337 |
| 3 | H | -CH₂-C₆H₄-OMe (meta) | Me | | 337 |

-continued
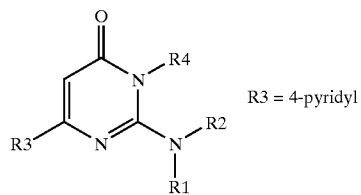
R3 = 4-pyridyl
| No. | R1 | R2 | R4 | m.p. (° C.) | [M + H]+ |
|---|---|---|---|---|---|
| 4 | H | 2-methoxyphenethyl | Me | 149.2–149.5 | 337 |
| 5 | H | 2-fluorophenethyl | Me | 184.0–187.2 | 325 |
| 6 | H | 3-fluorophenethyl | Me | 158.9–159.2 | 325 |
| 7 | H | 4-fluorophenethyl | Me | 178.8–178.9 | 325 |
| 8 | H | 4-bromophenethyl | Me | 192.2–192.3 | 386 |
| 9 | H | 2-chlorophenethyl | Me | 175.2–175.4 | 341 |
| 10 | H | 2,4-dichlorophenethyl | Me | 189.5–189.7 | 376 |
| 11 | H | 4-aminophenethyl | Me | 197.3–197.5 | 322 |
| 12 | H | 3,4-dimethoxyphenethyl | Me | 187.0–187.1 | 367 |

-continued
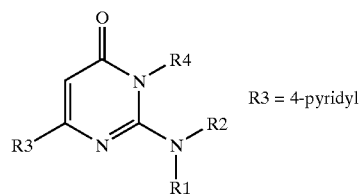
R3 = 4-pyridyl
| No. | R1 | R2 | R4 | m.p. (° C.) | [M + H]+ |
|---|---|---|---|---|---|
| 13 | H | 2,5-dimethoxyphenethyl | Me | 180.9–181.3 | 367 |
| 14 | H | 4-chlorophenethyl | Me | 165.3–165.5 | 341 |
| 15 | H | 4-hydroxyphenethyl | Me | 257.4–257.9 | 323 |
| 16 | H | 4-methylphenethyl | Me | 184.7–185 | 321 |
| 17 | H | 4-sulfamoylphenethyl | Me | — | 386 |
| 18 | H | 3-chlorophenethyl | Me | 162.8–163 | 341 |
| 19 | H | 2-(thiophen-2-yl)ethyl | Me | 171.7–171.9 | 313 |
| 20 | H | 4-phenylbutyl | Me | — | 335 |
| 21 | H | 4-benzyloxyphenethyl | Me | 169.7–169.8 | 413 |

-continued
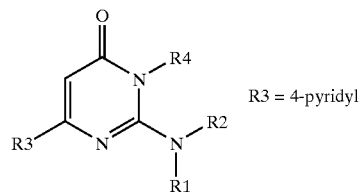
R3 = 4-pyridyl
| No. | R1 | R2 | R4 | m.p. (° C.) | [M + H]⁺ |
|---|---|---|---|---|---|
| 22 | H | 4-biphenylethyl | Me | 175.4–175.6 | 383 |
| 23 | H | phenylpropyl | Me | — | 293 |
| 24 | H | 2-methoxybenzyl-ethyl | Me | — | 323 |
| 25 | Me | 2,5-dimethoxyphenylethyl | Me | — | 381 |
| 26 | H | 3-(3-aminopropoxy)phenylethyl | Me | 193–196 (*) | — |
| 27 | H | 3-(aminomethyl)phenylethyl | Me | 193–197 (*) | — |
| 28 | H | phenylpropyl | CH₂—Ph | 218–221 | — |
| 29 | H | indol-3-ylethyl | Me | 217–218 (□) | 346 |
| 30 | H | 5-methoxyindol-3-ylpropyl | Me | 242.7–243.0 | 376 |

-continued
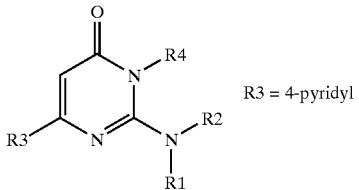
R3 = 4-pyridyl
| No. | R1 | R2 | R4 | m.p. (° C.) | [M + H]+ |
|---|---|---|---|---|---|
| 31 | H | 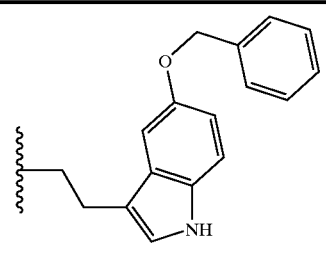 | Me | 168.4–168.6 | 452 |
| 32 | H | 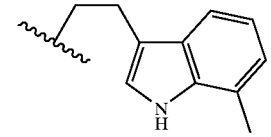 | Me | 217.2–217.3 | 360 |
| 33 | H | 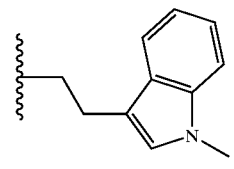 | Me | — | 360 |
| 34 | Me | 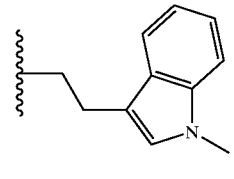 | Me | — | 374 |
| 35 | H | 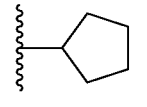 | Me | — | 271 |
| 36 | H | Et | Me | 239–241 (□) | 231 |
| 37 | H | 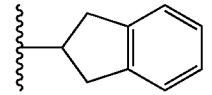 | Me | 211.5–211.8 | 319 |
| 38 | | —(CH$_2$)$_5$— | Me | 228–230 (***) | 271 |
| 39 | | —(CH$_2$)$_4$— | Me | — | 257 |
| 40 | H | 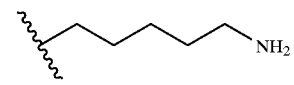 | Me | 259–262(*) | |
| 41 | H | 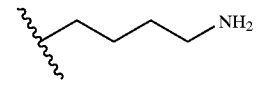 | 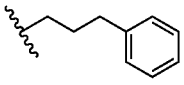 | 134–136(*) | |
| 42 | H | 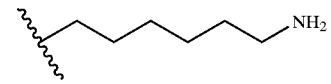 | 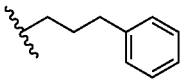 | 142–143(*) | |

-continued
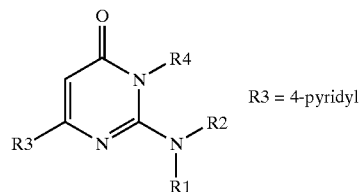
R3 = 4-pyridyl
| No. | R1 | R2 | R4 | m.p. (° C.) | [M + H]+ |
|---|---|---|---|---|---|
| 43 | H | ~(CH2)5~NH2 | ~CH2CH2-Ph | 235–238(*) | |
| 44 | H | ~(CH2)6~NH2 | ~CH2CH2-Ph | 225–228(*) | |
| 45 | H | ~(CH2)4~NH2 | ~CH2CH2-Ph | 246–248(*) | |
| 46 | H | ~cyclohexyl | Me | 268–270 | |
| 47 | H | ~n-butyl | Me | 180–182 | |
| 48 | H | ~n-pentyl | Me | 157–159 | |
| 49 | H | ~n-hexyl | Me | 133–135 | |
| 50 | H | ~n-heptyl | Me | 121–123 | |
| 51 | H | ~n-octyl | Me | 114–116 | |
| 52 | H | ~n-nonyl | Me | 113–115 | |
| 53 | H | ~n-decyl | Me | 162–164(**) | |
| 54 | H | ~CH2CH2-cyclohexyl | Me | 146–150 | |

-continued
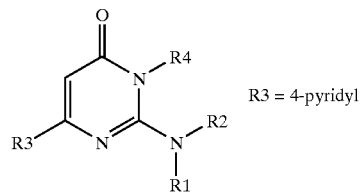
R3 = 4-pyridyl
| No. | R1 | R2 | R4 | m.p. (° C.) [M + H]+ |
|---|---|---|---|---|
| 55 | H | isopentyl | Me | 213–217 |
| 56 | H | cyclohexylmethyl | Me | 218–220 |
| 57 | H | -CH2CH2-O-CH2CH2CH3 | Me | 147–150 |
| 58 | H | 3-cyclohexylpropyl | Me | 177–180 |
| 59 | H | -CH2CH2CH2-O-CH2CH3 | Me | 118–120 |
| 60 | phenethyl | -(CH2)6-NH2 | Me | 158–162(*) |
| 61 | H | -(CH2)5-OH | Me | 164–165 |
| 62 | H | -(CH2)4-OH | Me | 159–161 |
| 63 | H | -CH2CH2CH2-O-CH(CH3)2 | Me | 95–98 |
| 64 | H | -CH2CH2CH2-O-CH2CH2CH3 | Me | 107–109 |
| 65 | H | -CH2-CH(OH)-Ph | Me | 202–206 |

-continued
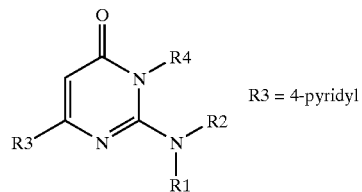
R3 = 4-pyridyl
| No. | R1 | R2 | R4 | m.p. (° C.) [M + H]+ |
|---|---|---|---|---|
| 66 | H | cyclopentylpropyl | Me | 190–194 |
| 67 | H | 3-(piperidin-1-yl)propyl | Me | 162–163 |
| 68 | Me | 3-cyclohexylpropyl | Me | 188–191(**) |
| 69 | H | 1-phenyl-1-acetoxypropyl | Me | 81–84 |
| 70 | H | 2-(adamantan-1-yl)ethyl | Me | 107–111 |
| 71 | H | 3-[3-(3-hydroxypropoxy)phenyl]propyl | Me | 98–101 |
| 72 | H | 3-{3-[2-(piperidin-4-yl)ethoxy]phenyl}propyl | Me | 225–232(*) |
| 73 | H | 3-[3-(3-acetoxypropoxy)phenyl]propyl | Me | 198–201 |
| 74 | H | 3-[3-(3-dimethylaminopropoxy)phenyl]propyl | Me | 80–82 |

-continued

R3 = 4-pyridyl

| No. | R1 | R2 | R4 | m.p. (° C.) [M + H]+ |
|---|---|---|---|---|
| 75 | Me | -CH2-C6H4-CH2-NH-CH3 (para) | Me | 157–160(*) |
| 76 | -CH2CH2-C6H5 | -(CH2)4-NH2 | Me | 210–213(**) |
| 77 | H | -(CH2)3-C6H5 | -(CH2)3-NH2 | 185–189(*) |
| 78 | H | -(CH2)3-C6H5 | Me | 122–124 |
| 79 | H | -(CH2)3-C6H5 | -(CH2)4-NH2 | 123–126(*) |
| 80 | H | -(CH2)3-C6H5 | -(CH2)4-NH2 | 124–127(*) |
| 81 | H | -CH2-C6H4-O-(CH2)3-(4-pyridyl) (meta) | Me | 210–213(*) |
| 82 | H | -(CH2)3-C6H5 | -(CH2)6-NH2 | 192–195(*) |
| 83 | H | -(CH2)3-C6H5 | -(CH2)5-NH2 | 125–127(*) |
| 84 | H | -(CH2)3-C6H5 | -(CH2)2-NH2 | 145–148(*) |

-continued
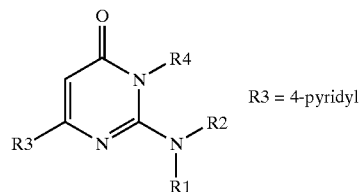
R3 = 4-pyridyl
| No. | R1 | R2 | R4 | m.p. (° C.) [M + H]+ |
|---|---|---|---|---|
| 85 | H | ⟋⟍-(2-methoxyphenyl)propyl | ⟋⟍-(CH2)3NH2 | 198–201(*) |
| 86 | H | ⟋⟍-(phenyl)propyl | ⟋⟍-(CH2)3OH | 143–145 |
| 87 | H | ⟋⟍-(phenyl)propyl | ⟋⟍-(CH2)2N(CH3)2 | 212–215(*) |
| 88 | H | ⟋⟍-(phenyl)ethyl | ⟋⟍-(CH2)5NH2 | 178–180(*) |
| 89 | H | ⟋⟍-(phenyl)ethyl | ⟋⟍-(CH2)4NH2 | 170–175(*) |
| 90 | H | ⟋⟍-(CH2)4NH2 | ⟋⟍-CH2-phenyl | 163–168dec(*) |
| 91 | H | ⟋⟍-(CH2)6NH2 | ⟋⟍-CH2-phenyl | 292–298(*) |
| 92 | H | ⟋⟍-CH2CH2-S-phenyl | Me | 162–168 |
| 93 | H | ⟋⟍-CH2CH2-NH-phenyl | Me | 102–105 |
| 94 | H | ⟋⟍-CH2CH2-O-phenyl | Me | 193–194 |

-continued

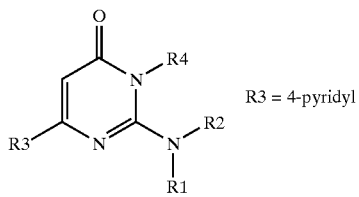

| No. | R1 | R2 | R4 | m.p. (° C.) | [M + H]+ |
|---|---|---|---|---|---|
| 95 | H | (E)-3-phenylallyl | Me | 198–200(**) | |
| 96 | H | 3-phenylpropyl | Me | 187–189(**) | |
| 97 | H | 2-(pyridin-2-yl)ethyl | Me | 154–156dec | |

All compounds are bases, except (*): dihydrochloride, (): monohydrochloride, (□): oxalate and (*): tartrate Test Example Inhibitory Activity of the Medicament of the Present Invention Against GSK3β

Two different protocols can be used.

In a first protocol: 7.5 μM of prephosphorylated GS1 peptide and 10 μM ATP (containing 300,000 cpm of 33P-ATP) were incubated in 25 mM Tris-HCl, pH 7.5, 0.6 mM DTT, 6 mM MgCl$_2$, 0.6 mM EGTA, 0.05 mg/ml BSA buffer for 1 hour at room temperature in the presence of GSK3β (total reaction volume: 100 microliters).

In a second protocol: 4.1 μM of prephosphorylated GS1 peptide and 42 μM ATP (containing 260,000 cpm 33P-ATP) were incubated in 80 mM Mes-NaOH, pH 6.5, 1 mM Mg acetate, 0.5 mM EGTA, 5 mM 2-mercaptoethanol, 0.02% Tween 20, 10% glycerol buffer for 2 hours at room temperature in the presence of GSK3β. Inhibitors were solubilised in DMSO (final solvent concentration in the reaction medium, 1%).

The reaction was stopped with 100 microliters of a solution made of 25 g polyphosphoric acid (85% P$_2$O$_5$), 126 ml 85% H$_3$PO$_4$, H$_2$O to 500 ml and then diluted to 1:100 before use. An aliquot of the reaction mixture was then transferred to Whatman P81 cation exchange filters and rinsed with the solution described above. Incorporated 33P radioactivity was determined by liquid scintillation spectrometry.

The phosphorylated GS-1 peptide had the following sequence: NH2-YRRAAVPPSPSLSRHSSPHQS(P)EDEE-COOH.

The GSK3β inhibitory activity of the compounds of the present invention are expressed in IC$_{50}$, and as an illustration the range of IC$_{50}$'s of the compounds in table 1 is between 0.1 to 10 micromolar concentrations.

Formulation Example (1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

(1) Parenteral Preparations

The ingredients below were mixed by an ordinary method to prepare injections contained in a 1 ml ampoule.

| | |
|---|---|
| Compound of Example 1 | 3 mg |
| Sodium chloride | 4 mg |
| Distilled water for injection | 1 ml |

INDUSTRIAL APPLICABILITY

The compounds of the present invention have GSK3β inhibitory activity and are useful as an active ingredient of a medicament for preventive and/or therapeutic treatment of neurodegenerative diseases caused by abnormal activity of GSK3β.

What is claimed is:

1. A compound of formula (I):

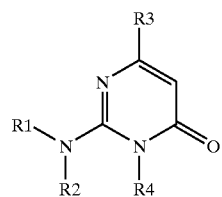

wherein:

R1 and R2 together form a $C_{2-6}$ alklene group which may be substituted;

R3 represents a 2, 3 or 4-pyridyl group optionally substituted by a $C_{1-4}$ alkyl group, $C_{1-4}$ alkoxy group or a halogen atom; and R4 represents a $C_{1-10}$ alkyl group optionally substituted by a hydroxyl, amino, $C_{1-6}$ monoalkylamino, $C_{2-12}$ dialkylamino, or $C_{6-10}$ aryl group which may be substituted; or a salt, solvate or hydrate thereof.

2. A compound selected from the group consisting of:

2-[[2-(phenyl)ethyl]amino]-3-methyl-6-pyridin-4-ylpyrimidin-4(3H)-one,

2-[[2-(4-methoxyphenyl)ethyl]amino]-3-methyl-6-pyridin-4-ylpyrimidin-4(3H)-one,

2-[[2-(3methoxyphenyl)ethyl]amino]-3-methyl-6-pyridin-4-ylpyrimidin-4(3H)-one,

2-[[2-(2-methoxyphenyl)ethyl]amino]-3-methyl-6-pyridin-4-ylpyrimidin-4(3H)-one,

2-[[2-(2-fluorophenyl)ethyl]amino]-3-methyl-6-pyridin-4-ylpyrimidin-4(3H)-one,

2-[[2-(3-fluorophenyl)ethyl]amino]-3-methyl-6-pyridin-4-ylpyrimidin-4(3H)-one,

2-[[2-(4-fluorophenyl)ethyl]amino]-3-methyl-6-pyridin-4-ylpyrimidin-4(3H)-one,

2-[[2-(4-bromophenyl)ethyl]amino]-3-methyl-6-pyridin-4-ylpyrimidin-4(3H)-one,

2-[[2-(2-chlorophenyl)ethyl]amino]-3-methyl-6-pyridin-4-ylpyrimidin-4(3H)-one,

2-[[2-(2,4-dichlorophenyl)ethyl]amino]-3-methyl-6-pyridin-4-ylpyrimidin-4(3H)-one, 2-[[2-(4-aminophenyl)ethyl]amino]-3-methyl-6-pyridin-4-ylpyrimidin-4(3H)-one, 2-[[2-(3,4-dimethoxyphenyl)ethyl]amino]-3-methyl-6-pyridin-4-ylpyrimidin-4(3H)-one, 2-[[2-(2,5-dimethoxyphenyl)ethyl]amino]-3-methyl-6-pyridin-4-ylpyrimidin-4(3H)-one, 2-[[2-(4-chlorophenyl)ethyl]amino]-3-methyl-6-pyridin-4-ylpyrimidin-4(3H)-one, 2-[[2-(4-hydroxyphenyl)ethyl]amino]-3-methyl-6-pyridin-4-ylpyrimidin-4(3H)-one, 2-[[2-(4-methylphenyl)ethyl]amino]-3-methyl-6-pyridin-4-ylpyrimidin-4(3H)-one, 2-[[2-(4-aminosulfonylphenyl)ethyl]amino]-3-methyl-6-pyridin-4-ylpyrimidin-4(3H)-one, 2-[[2-(3-chlorophenyl)ethyl]amino]-3-methyl-6-pyridin-4-ylpyrimidin-4(3H)-one, 2-[[2-(thiophen-2-yl)ethyl]amino]-3-methyl-6-pyridin-4-ylpyrimidin-4(3H)-one, 2-[[4-(phenyl)butyl]amino]-3-methyl-6-pyridin-4-ylpyrimidin-4(3H)-one, 2-[[2-(4-phenylmethoxyphenyl)ethyl]amino]-3-methyl-6-pyridin-4-ylpyrimidin-4(3H)-one, 2-[[2-(4-phenylphenyl)ethyl]amino]-3-methyl-6-pyridin-4-ylpyrimidin-4(3H)-one, 2-[(phenylmethyl)amino]-3-methyl-6-pyridin-4-ylpyrimidin-4(3H)-one, 2-[[(2-methoxyphenyl)methyl]amino]-3-methyl-6-pyridin-4-ylpyrimidin-4(3H)-one, 2-[[2-(2,5-dimethoxyphenyl)ethyl]methylamino]-3-methyl-6-pyridin-4-ylpyrimidin-4(3H)-one, 2-[[[3-(3-aminopropoxy)phenyl]methyl]amino]-3-methyl-6-pyridin-4-ylpyrimidin-4(3H)-one, 2-[[[3-(aminomethyl)phenyl]methyl]amino]-3-methyl-6-pyridin-4-ylpyrimidin-4(3H)-one, 2-[[3-(phenyl)propyl]amino]-3-phenylmethyl-6-pyridin-4-ylpyrimidin4(3H)-one, 2-[[2-(1H-indol-3-yl)ethyl]amino]-3-methyl-6-pyridin-4-ylpyrimidin-4(3H)-one, 2-[[2-(5-methoxy-1H-indol-3-yl)ethyl]amino]-3-methyl-6-pyridin-4-ylpyrimidin-4(3H)-one, 2-[[2-(5-phenylmethoxy-1H-indol-3-yl)ethyl]amino]-3-methyl-6-pyridin-4-ylpyrimidin-4(3H)-one, 2-[[2-(7-methyl-1H-indol-3-yl)ethyl]amino]-3-methyl-6-pyridin-4-yl pyrimidin-4-(3H)-one, 2-[[2-(1-methyl-1H-indol-3-yl)ethyl]amino]-3-methyl-6-pyridin-4-ylpyrimidin-4(3H)-one, 2-[[2-(1-methyl-1H-indol-3-yl)ethyl]methylamino]-3-methyl-6-pyridin-4-ylpyrimidin-4(3H)-one, 2-(cyclopentylamino)-3-methyl-6-pyridin-4-ylpyrimidin-4(3H)-one, 2-(ethylamino)-3-methyl-6-pyridin-4-ylpyrimidin-4(3H)-one, 2-[(indan-2-yl)amino]-3-methyl-6-pyridin-4-ylpyrimidin-4(3H)-one, 2-(piperidin-1-yl)-3-methyl-6-pyridin-4-ylpyrimidin-4 (3H)-one, 2-(pyrrolidin-1-yl)-3-methyl-6-pyridin-4-ylpyrimidin-4 (3H)-one, 2-(5-Amino-pentylamino)-3-methyl-6-pyridin-4-yl-3H-pyrimidin-4-one, 2-(4-Amino-butylamino)-3-(3-phenyl-propyl)-6-pyridin-4-yl-3H-pyrimidin-4-one, 2-(6-Amino-hexylamino)-3-(3-phenyl-propyl)-6-pyridin-4-yl-3H-pyrimidin-4-one, 2-(5-Amino-pentylamino)-3-phenylethyl-6-pyridin-4-yl-3H-pyrimidin-4-one, 2-(6-Amino-hexylamino)-3-phenethyl-6-pyridin-4-yl-3H-pyrimidin-4-one, 2-(4-Amino-butylamino)-3-phenethyl-6-pyridin-4-yl-3H-pyrimidin-4-one, 2-Cyclohexylamino-3-methyl-6-pyridin-4-yl-3H-pyrimidin-4-one, 2-Butylamino-3-methyl-6-pyridin-4-yl-3H-pyrimidin-4-one, 3-Methyl-2-pentylamino-6-pyridin-4-yl-3H-pyrimidin-4-one, 2-Hexylamino-3-methyl-6-pyridin-4-yl-3H-pyrimidin-4-one, 2-Heptylamino-3-methyl-6-pyridin-4-yl-3H-pyrimidin-4-one, 3-Methyl-2-octylamino-6-pyridin-4-yl-3H-pyrimidin-4-one,
3-Methyl-2-nonylamino-6-pyridin-4-yl-3H-pyrimidin-4-one,
2-Decylamino-3-methyl-6-pyridin-4-yl-3H-pyrimidin-4-one,
2-(2-Cyclohexyl-ethylamino)-3-methyl-6-pyridin-4-yl-3H-pyrimidin-4-one,
3-Methyl-2-(3-methyl-butylamino)-6-pyridin-4-yl-3H-pyrimidin-4-one,
2-(Cyclohexylmethyl-amino)-3-methyl-6-pyridin-4-yl-3H-pyrimidin-4-one,
3-Methyl-2-(2-propoxy-ethylamino)-6-pyridin-4-yl-3H-pyrimidin-4-one,
2-(3-Cyclohexyl-propylamino)-3-methyl-6-pyridin-4-yl-3H-pyrimidin-4-one,
2-(3-Ethoxy-propylamino)-3-methyl-6-pyridin-4-yl-3H-pyrimidin-4-one,
2-[(5-Amino-pentyl)-phenetyl-amino]-3-methyl-6-pyridin-4-yl-3H-pyrimidin-4-one,
2-(5-Hydroxy-pentylamino)-3-methyl-6-pyridin-4-yl-3H-pyrimidin-4-one,
2-(4-Hydroxy-butylamino)-3-methyl-6-pyridin-4-yl-3H-pyrimidin-4-one,
2-(3-Isopropoxy-propylamino)-3-methyl-6-pyridin-4-yl-3H-pyrimidin-4-one,
3-Methyl-2-(3-propoxy-propylamino)-6-pyridin-4-yl-3H-pyrimidin-4-one,
2-(2-Hydroxy-2-phenyl-ethylamino)-3-methyl-6-pyridin-4-yl-3H-pyrimidin-4-one,
2-(2-Cyclopentyl-ethylamino)-3-methyl-6-pyridin-4-yl-3H-pyrimidin-4-one,
3-Methyl-2-(3-piperidin-1-yl-propylamino)-6-pyridin-4-yl-3H-pyrimidin-4-one,
2-[(3-Cyclohexyl-propyl)-methyl-amino]-3-methyl-6-pyridin-4-yl-3H-pyrimidin-4-one,
Acetic acid 2-(1-methyl-6-oxo-4-pyridin-4-yl-1,6-dihydro-pyrimidin-2-ylamino)-1-phenyl-ethyl ester
2-(2-Adamantan-1-yl-ethylamino)-3-methyl-6-pyridin-4-yl-3H-pyrimidin-4-one,
2-[3-(3-Hydroxy-propoxy)-benzylamino]-3-methyl-6-pyridin-4-yl-3H-pyrimidin-4-one,
3-methyl-2-[3-(2-piperidin-4-yl-ethoxy)-benzylamino]-6-pyridin-4-yl-3H-pyrimidin-4-one,
Acetic acid 3-{3-[(1-methyl-6-oxo-4-pyridin-4-yl-1,6-dihydro-pyrimidin-2-ylamino)-methyl]-phenoxy}-propyl ester
2-[3-(3-Dimethylamino-propoxy)-benzylamino]-3-methyl-6-pyridin-4-yl-3H-pyrimidin-4-one,
3-Methyl-2-{methyl-[2-(4-methylaminomethyl-phenyl)-ethyl]-amino}-6-pyridin-4-yl-3H-pyrimidin-4-one,
2-[(4-Amino-butyl)-phenethyl-amino]-3-methyl-6-pyridin-4-yl-3H-pyrimidin-4-one,
2-(3-Amino-propyl)-(3-phenyl-propyl)-amino)-6-pyridin-4-yl-3H-pyrimidin-4-one,
3-Methyl-2-(3-phenyl-propylamino)-6-pyridin-4-yl-3H-pyrimidin-4-one,
3-(5-Amino-pentyl)-2-(3-phenyl-propylamino)-6-pyridin-4-yl-3H-pyrimidin-4-one,
3-(4-Amino-butyl)-2-(3-phenyl-propylamino)-6-pyridin-4-yl-3H-pyrimidin-4-one,
3-Methyl-6-pyridin-4-yl-2-[3-(3-pyridin-4-yl-propoxy)-benzylamino]-3H-pyrimidin-4-one,
3-(6-Amino-hexyl)-2-(3-phenyl-propylamino)-6-pyridin-4-yl-3H-pyrimidin-4-one,
3-(6-Amino-hexyl)-2-phenethylamino-6-pyridin-4-yl-3H-pyrimidin-4-one,
3-(2-Amino-ethyl)-2-(3-phenyl-propylamino)-6-pyridin-4-yl-3H-pyrimidin-4-one,
3-(3-Amino-propyl)-2-[2-(2-methoxy-phenyl)-ethylamino]-6-pyridin-4-yl-3H-pyrimidin-4-one,
3-(2-Hydroxy-ethyl)-2-(3-phenyl-propylamino)-6-pyridin-4-yl-3H-pyrimidin-4-one,
3-(2-Dimethylamino-ethyl)-2-(3-phenyl-propylamino)-6-pyridin-4-yl-3H-pyrimidin-4-one,
3-(5-Amino-pentyl)-2-phenethylamino-6-pyridin-4-yl-3H-pyrimidin-4-one,
3-(4-Amino-butyl)-2-phenethylamino-6-pyridin-4-yl-3H-pyrimidin-4-one,
2-(4-Amino-butylamino)-3-benzyl-6-pyridin-4-yl-3H-pyrimidin-4-one,
2-(6-Amino-hexylamino)-3-benzyl-6-pyridin-4-yl-3H-pyrimidin-4-one,
3-Methyl-2-(2-phenylsulfanyl-ethylamino)-6-pyridin-4-yl-3H-pyrimidin-4-one,
3-Methyl-2-(2-phenylamino-ethylamino)-6-pyridin-4-yl-3H-pyrimidin-4-one,
3-Methyl-2-(2-phenoxy-ethylamino)-6-pyridin-4-yl-3H-pyrimidin-4-one,
3-Methyl-2-(3-phenyl-allylamino)-6-pyridin-4-yl-3H-pyrimidin-4-one,
3-Methyl-2-(3-phenyl-propylamino)-6-pyridin-4-yl-3H-pyrimidin-4-one, and
3-Methyl-6-pyridin-4-yl-2(2-pyridin-2-yl-ethylamino)-3H-pyrimidin-4-one or a salt thereof, or a solvate thereof or a hydrate thereof.

3. A pharmaceutical composition comprising a compound according to claim 1 together with a pharmaceutically acceptable excipient.

4. A pharmaceutical composition comprising a compound according to claim 2 together with a pharmaceutically acceptable excipient.

* * * * *